United States Patent [19]

Lässig et al.

[11] 4,366,240
[45] Dec. 28, 1982

[54] COLOR PHOTOGRAPHIC RECORDING MATERIAL CONTAINING NON-DIFFUSING ELECTRON DONOR PRECURSOR COMPOUNDS

[75] Inventors: Wolfgang Lässig; Ernst Meier; Siegfried Schleger, all of Munich, Fed. Rep. of Germany

[73] Assignee: Agfa-Gevaert Aktiengesellschaft, Leverkusen, Fed. Rep. of Germany

[21] Appl. No.: 234,880

[22] Filed: Feb. 17, 1981

[30] Foreign Application Priority Data

Feb. 20, 1980 [DE] Fed. Rep. of Germany ....... 3006268

[51] Int. Cl.$^3$ ...................... G03C 5/54; G07C 49/62; G09B 53/00
[52] U.S. Cl. ................................... 430/542; 430/223; 430/242; 430/440; 430/483
[58] Field of Search ............... 430/223, 242, 440, 483, 430/542, 566

[56] References Cited

U.S. PATENT DOCUMENTS 4,139,379   2/1979   Chasman ............................ 430/223

Primary Examiner—John E. Kittle
Assistant Examiner—John L. Goodrow
Attorney, Agent, or Firm—Connolly and Hutz

[57] ABSTRACT

5- or 6-membered α-lactones of phenolic compounds, in which the phenyl ring carries a hydroxyl or amino group in its 2- or 4-position to the lactonized phenolic hydroxyl group and in which the lactone ring carries an electron accepting substituent, so that the lactone ring is readily cleavable at pH values of from 10 to 13 to form an electron donor compound (ED-compound) having a redox potential of less than +0.255 V determined against a normal calomel electrode at pH 0 are useful ED precursor compounds for non-diffusing reducible color providing compounds.

7 Claims, No Drawings

COLOR PHOTOGRAPHIC RECORDING MATERIAL CONTAINING NON-DIFFUSING ELECTRON DONOR PRECURSOR COMPOUNDS

This invention relates to a color photographic recording material having at least one light-sensitive silver halide emulsion layer containing non-diffusing electron donor precursor compounds from which powerful reducing agents are formed under alkaline development conditions. The invention relates in particular to a recording material in which the aforesaid electron donor precursor compounds are used in combination with non-diffusing reducible, color providing compounds which in their reduced state and under alkaline development conditions release diffusible dyes which as such or after they have been converted to their corresponding metal complex dyes, contribute to the image formation. The invention also relates to new compounds suitable as electron donor precursor compounds.

Color providing compounds which contain an electron accepting nucleophilic precursor group and which, in their reduced state, undergo an intramolecular nucleophilic displacement reaction under alkaline development conditions to release a diffusible dye have been described in German Offenlegungsschrift No. 2,809,716. Reduction is effected by so-called electron donor compounds (ED compounds) which are present in the layers in addition to the color providing compounds and which are oxidized imagewise by development and thereby used up.

The remaining ED compounds which are distributed imagewise (positive residual image) react with the color providing compounds to release diffusible dyes in imagewise distribution. The ED compounds described there include, for example, derivatives of benzisoxazolone, of hydroquinone, of hydroquinone, of p-aminophenol and of ascorbic acid. In order to produce high quality images by the process described in German Offenlegungsschrift No. 2,809,716, the ED compounds must not only be capable of being oxidized by exposed silver halide or by silver halide developer oxidation products but must themselves be capable of reducing the color providing compounds containing the electron accepting, nucleophilic precursor group. In addition, the velocities of the oxidation and reduction reactions must be optimally adjusted to each other so that the ED compound has already been oxidized to a significant extent during development before it is capable of reducing the color providing compound. The known ED compounds do not satisfy these requirements in all respects, and this defect may result in, for example, insufficient color density and/or an unacceptable color fog in the color transfer images produced. The high reduction capacity of suitable ED compounds goes hand-in-hand with a high sensitivity to oxidation which may result if the photographic recording material is stored for a considerable time, in premature non-imagewise destruction of the ED compounds by oxidation and consequently in poor image characteristics of the transfer image, such as insufficient color density. From German Offenlegungsschrift No. 2,809,716 it is also known to use the ED compound not as such but in the form of a precursor compound which is less sensitive to oxidation, and from which the ED compound proper is subsequently formed under the conditions of alkaline development. Examples of these include the ED compounds ED-8, ED-9 and ED-10 mentioned in the aforesaid German Offenlegungsschrift. When these known ED precursor compounds are used, however, the density of the color transfer image obtained within an acceptable development time is insufficient, presumably due to the fact that the ED compound is not formed sufficiently rapidly from the precursor compound or does not have a sufficient capacity for reduction.

It is an object of the present invention to indicate new ED precursor compounds which are resistant to oxidation and from which ED compounds having a high reduction capacity are formed under alkaline development conditions. It is particularly intended that these compounds should make it possible for color transfer images with improved color density to be obtained by the dye diffusion transfer process if they are used in combination with non-diffusing, reducible color providing compounds.

The present invention relates to a color photographic recording material having at least one light-sensitive silver halide emulsion layer and a non-diffusing electron donor precursor compound (ED precursor compound) associated therewith, from which precursor compound a non-diffusing ED compound having a high reduction capacity is formed under alkaline development conditions, the ED precursor compound obtained in the recording material being a 5-membered or 6-membered α-lactone of a phenol in which the phenyl ring carries a hydroxyl group or an amino group in its 2- or 4-position to the lactonized phenolic hydroxyl group, and the lactone ring contains electron accepting substituents which effect cleavage of the lactone ring at pH values of from 10 to 13. Furthermore, the cleavage of the lactone ring is determined in terms of half life values of the oxidative degradation of the lactone compound in two measurements carried out in a heterodisperse mixture of a solution of 20 mg of the ED precursor compound and 5 mg of 1-phenol-pyrazolidone-3 in 5 ml of n-butanol as finely divided organic base and a solution of 50 mg of potassium ferricyanide, 10 ml of water and 5 ml of a buffer solution at room temperature, the first measurement being carried out in the presence of a buffer solution consisting of 3.092 g of boric acid ($H_3BO_3$), 3.728 g of potassium chloride and 0.852 g of sodium hydroxide made up to 50 ml with water, and the second measurement being carried out in the presence of a buffer solution consisting of 3.728 g of potassium chloride and 1.884 g of sodium hydroxide made up to 50 ml with water, where the ED precursor compounds of the present invention have half life values of more than 10 minutes in the first measurement and half life values of less than 10 minutes in the second measurement. Further, the ED compound formed by decomposition of the lactone ring has a redox potential of less than +0.255, determined at pH 0 against a normal calomel electrode.

The hydroxyl or amino group in the 2- or 4-position to the lactonized phenolic hydroxyl group may be substituted by hydrolysable acyl groups. The amino group may also contain other substituents, such as one or two alkyl groups, preferably with up to 5 carbon atoms. Preferred ED precursor compounds are those of the benzofuranone series which are substituted in the lactone ring with electron accepting substituents of the following type: alkoxycarbonyl, in particular those containing alkoxy groups with up to 5 carbon atoms, phenoxycarbonyl, carbocyclic or heterocyclic aromatic substituents, in particular phenyl, diphenyl, pyridyl, thienyl, pyrryl, indolyl, imidazolyl, benzimidazolyl, oxazolyl or benzoxazolyl; cyano or acyl in which the acyl group is preferably derived from aryl carboxylic acids, such as benzoyl.

The problem according to the invention is solved in a particularly advantageous manner by a color photographic recording material having at least one light-sensitive silver halide emulsion layer and, associated with this layer, a non-diffusing electron donor precursor compound (ED precursor compound) from which a non-diffusing electron donor compound (ED compound) is formed under alkaline development conditions, which ED precursor compound corresponds to the following general formula

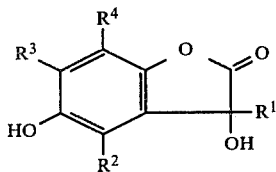

I in which
R$^1$ represents a carbocyclic or heterocyclic aromatic group;
R$^2$, R$^3$ and R$^4$ which may be the same or different substituents, represent hydrogen, alkyl, alkenyl, aryl, alkoxy, alkylthio and amino or
R$^3$ and R$^4$ together complete a condensed ring, in particular a carbocyclic ring,
and at least one of the substituents R$^1$, R$^2$, R$^3$ and R$^4$ contains a ballast group having 10–22 carbon atoms which confers diffusion resistance.

The ED precursor compounds according to the invention are suitable for use in color photographic recording materials wherever it is desired to introduce powerful reducing agents in a masked form into the layers, either as masked developer for silver halide or as masked reducing agent to prevent unwanted diffusion of oxidation products of silver halide development. It is immaterial what type of color providing compounds are used for producing the color image; they may be color couplers or color providing compounds which release diffusible dyes as a result of development. The preferred use of the ED precursor compounds according to the invention lies, however, in their combination with non-diffusing, reducible color providing compounds which in their reduced form are capable of releasing diffusible dyes under alkaline development conditions.

A preferred object of this invention is thus a color photographic recording material having at least one light-sensitive silver halide emulsion layer and, associated with this layer, a combination of a non-diffusing, reducible color providing compound which in its reduced state is capable of releasing a diffusible dye under alkaline development conditions, and a non-diffusing electron donor precursor compound (ED precursor compound) from which a non-diffusing electron donor compound (ED compound) is formed under alkaline development conditions, which ED compound is capable of reducing the non-diffusing color providing compound under alkaline development conditions, characterized in that the recording material contains a compound of the general formula I as ED precursor compound.

The invention also has as its object compounds corresponding to the general formula I (ED precursor compounds).

The aromatic ring represented by R$^1$ in formula I may be a carbocyclic ring, e.g. a phenyl, naphthyl or anthracene group, or a 5-membered or 6-membered heterocyclic ring having at least one of the hetero atoms N, O and S as ring member, e.g. an imidazolyl, thienyl, oxazolyl, pyrryl or pyridyl group. The carbocyclic and heterocyclic aromatic rings may be unsubstituted or carry one or more substituents and they may contain condensed carbocyclic or heterocyclic rings which in this case need not be aromatic.

The following are examples of suitable substituents on the aromatic rings represented by R$^1$ and on rings condensed thereto: Halogen such as fluorine, chlorine, bromine or iodine, hydroxyl, sulfo, sulfamoyl, trifluoromethylsulfonyl, amino, nitro, cyano, carboxyl, carbamoyl, alkoxycarbonyl, alkyl, alkenyl, cycloalkyl, in particular cyclohexyl or cyclopentyl, aryl, in particular phenyl, or heterocyclic groups; the last mentioned groups including the alkyl, alkenyl, cycloalkyl, aryl and heterocyclic groups may contain further substituents, e.g. those of the type already mentioned, and/or may be linked either directly or through one of the following divalent linking members: —O—, —S—, —SO$_2$—, —SO$_2$—NR—, —NR—SO$_2$—, —NR—CO—, —CO—NR, —NR—COO—, —O—CO—NR— and —NR—CO—NR— (R represents hydrogen or alkyl).

The alkyl or alkenyl groups contained in the substituents present in R$^2$, R$^3$ or R$^4$ or on the aromatic ring represented by R$^1$ may be straight or branched chain and contain from 1 to 22 carbon atoms.

An amino group represented by R$^2$, R$^3$ or R$^4$ or present as substituent in R$^1$ corresponds to the formula

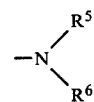

in which R$^5$ and R$^6$ which may be the same or different represent hydrogen, alkyl or aryl or the ring members required to complete a 5-membered or 6-membered cyclic amino group (Examples: pyrrolidino, piperidino, morpholino).

According to the invention, the totality of the substituents present in the ED precursor compound according to the invention is arranged so that the precursor compound can be incorporated in a non-diffusing form in photographic layers. This may be achieved by, for example, at least one of the substituents present, e.g. at least one of the groups, R$^1$, R$^2$, R$^3$ and R$^4$, or a substituent on a ring which is completed by at least two of the aforesaid groups, e.g. by R$^3$ and R$^4$, containing a group which confers diffusion resistance. Diffusion resistant incorporation of the ED precursor compound is particularly desirable because this compound is used in a certain quantitative proportion to the associated non-diffusing reducible, color providing compound, and this proportion should if possible not change significantly even during prolonged storage of the photographic recording material.

Groups may be regarded as conferring diffusion resistance if they make it possible for the compounds according to the invention to be incorporated in a diffusion-fast form in the hydrophilic colloids normally used in photographic materials. Particularly suitable for this purpose are organic groups generally containing straight chain or branched chain aliphatic groups and optionally also carbocyclic or heterocyclic aromatic groups generally having from 10 to 22 carbon atoms. These groups are attached to the remaining molecule either directly or indirectly, e.g. through one of the following groups: —NHCO—, —NHSO$_2$—, —NR— in which R represents hydrogen or alkyl, and —O— or —S—. The group which confers diffusion resistance may also contain groups which impart solubility in water, e.g. sulfo groups or carboxyl groups, and these may also be present in an anionic form. Since the diffusion properties depend on the molecular size of the total compound used, it is sufficient in some cases, e.g. when the molecule as a whole is large enough or when the ED precursor compounds are incorporated in the layers in an emulsified form by means of so-called oil formers or high boiling coupler solvents, to use relatively short chain groups such as isoamyl or tert.-butyl groups for conferring diffusion resistance.

The following are some examples of the non-diffusing ED precursor compounds used according to the invention.

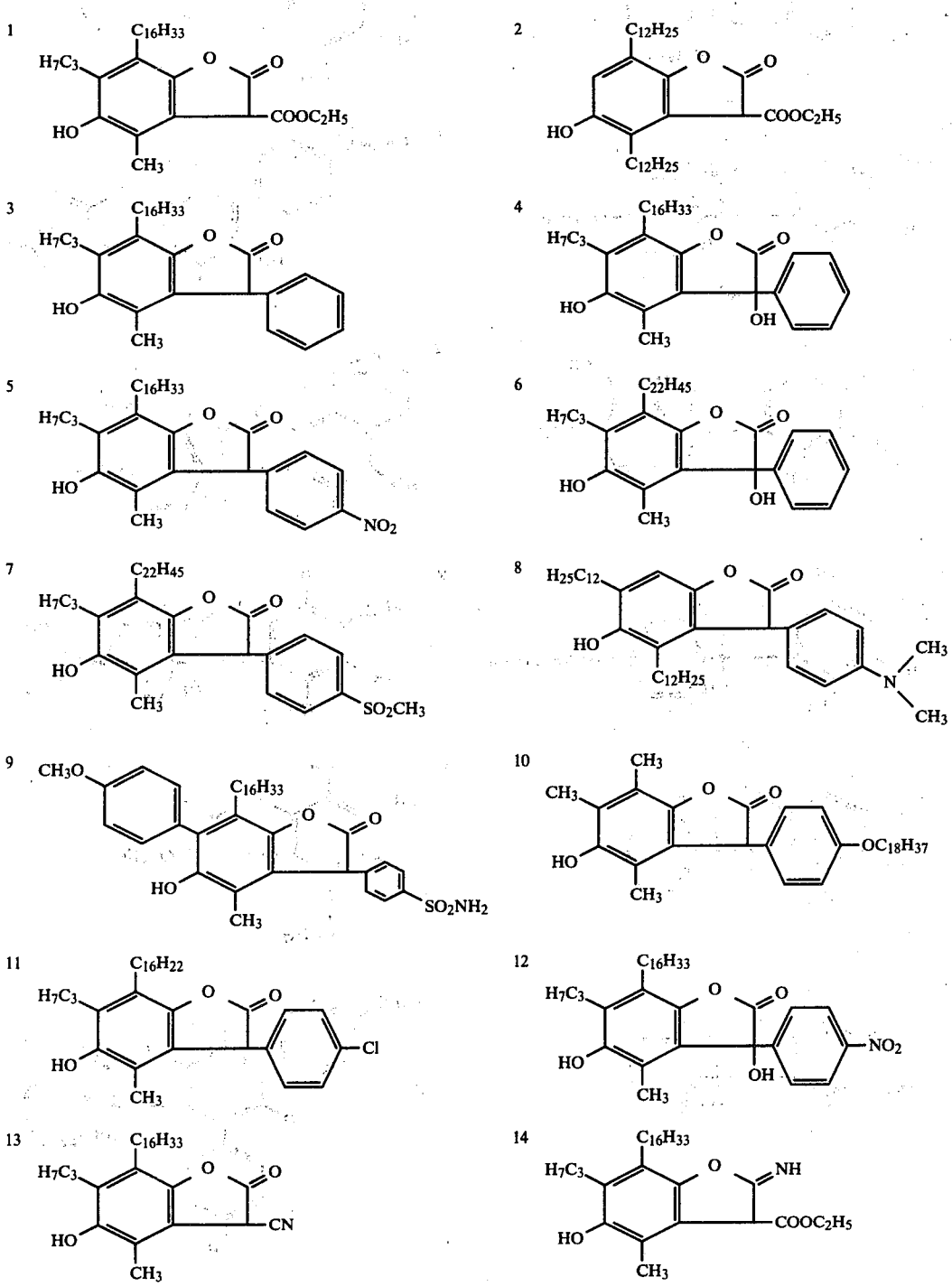

-continued
15 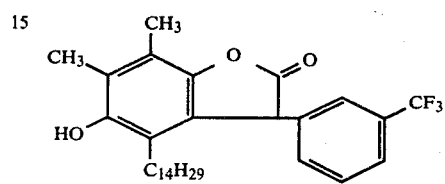
16 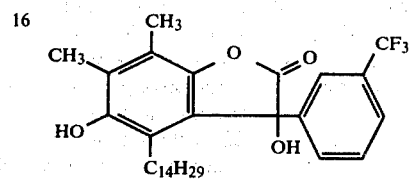
17 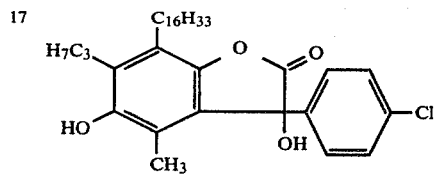
18 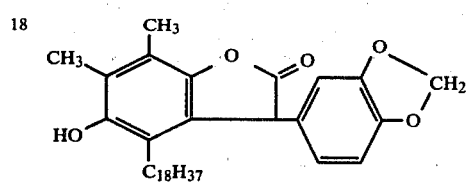
19 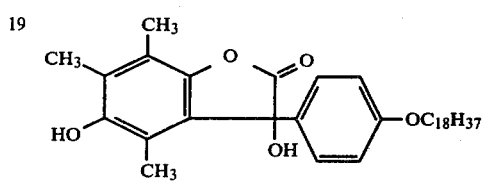
20 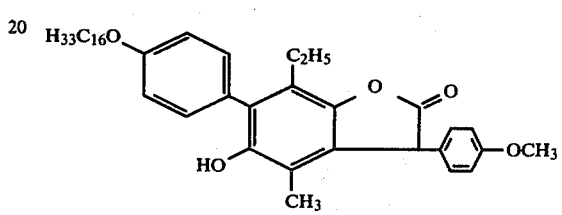
21 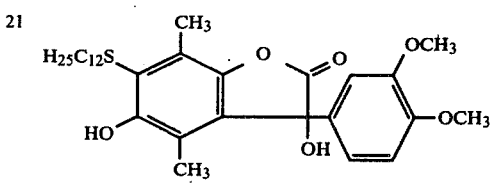
22 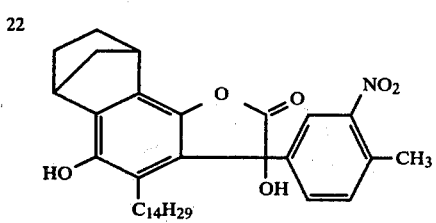
23 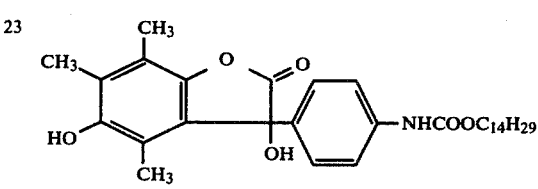
24 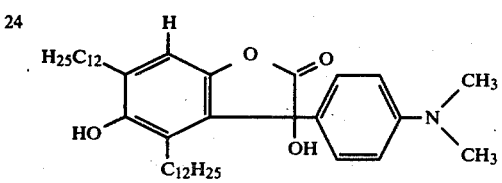
25 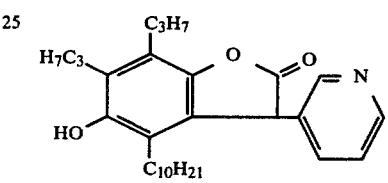
26 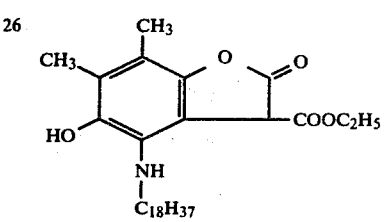
27 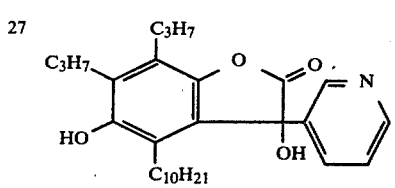
28 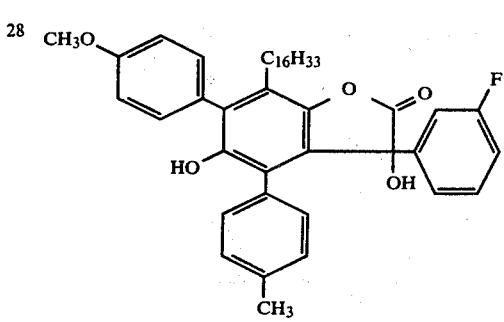

-continued
29 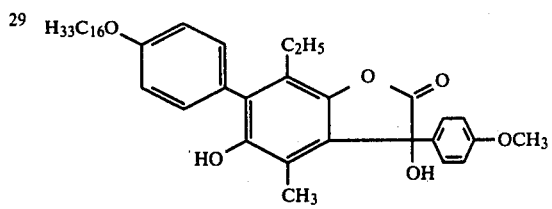
30 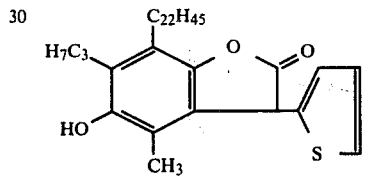
31 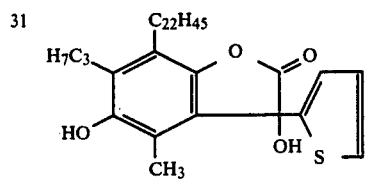
32 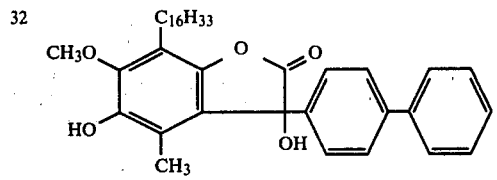
33 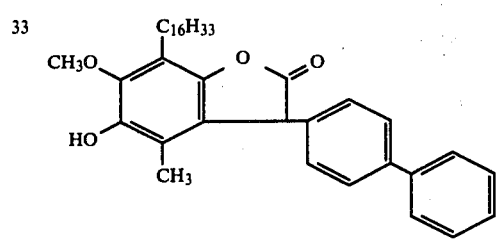
34 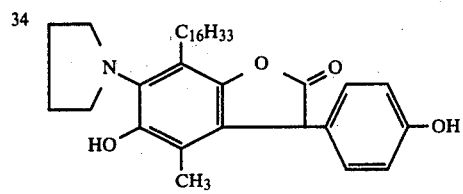
35 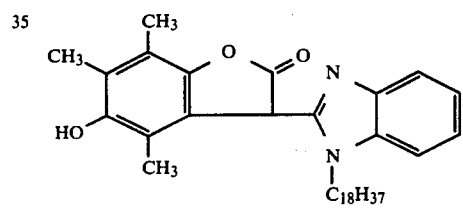
36 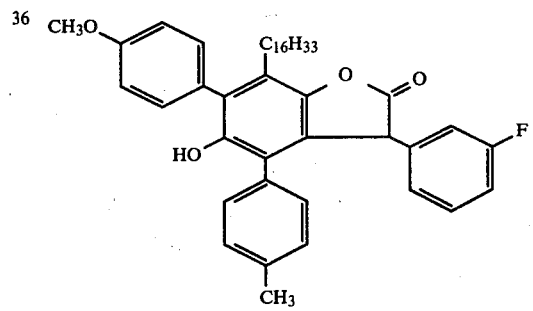
37 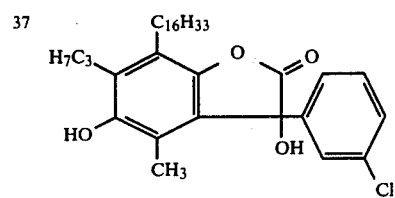
38 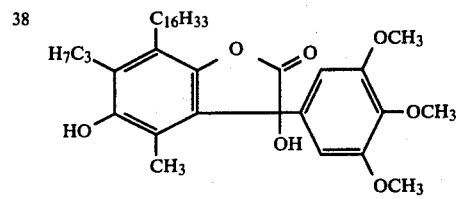
39 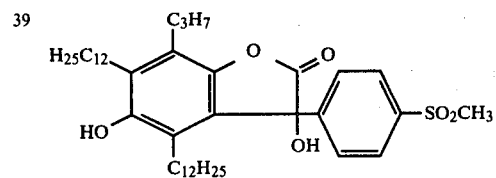
40 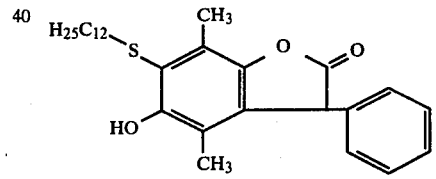
41 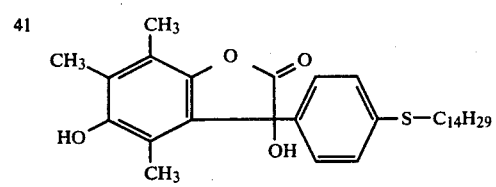
42 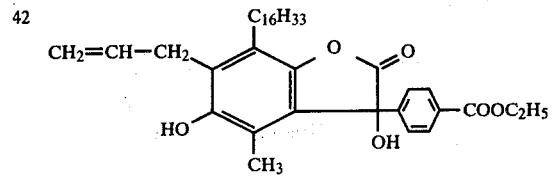

-continued
43 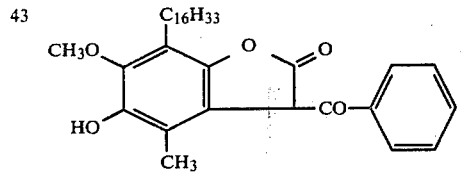
44 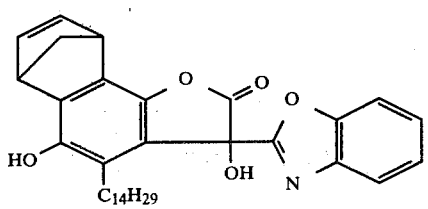
45 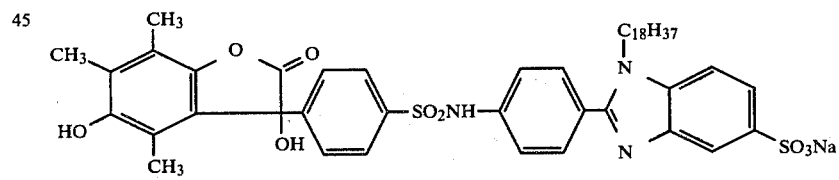
46 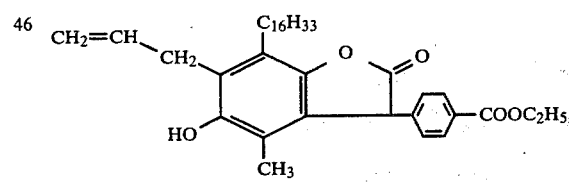
47 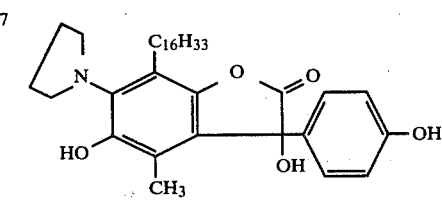
48 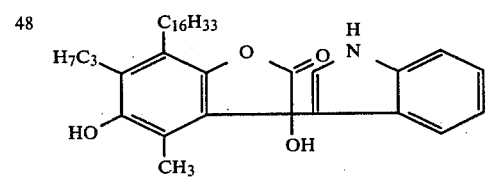
49 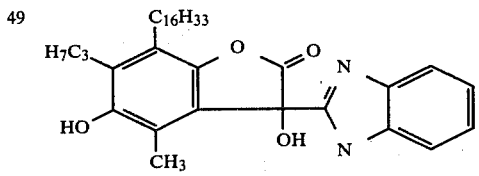
50 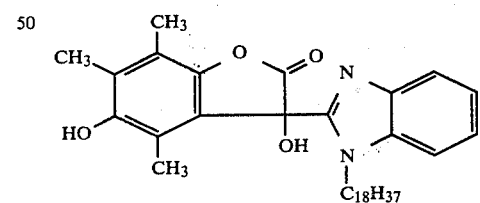
51 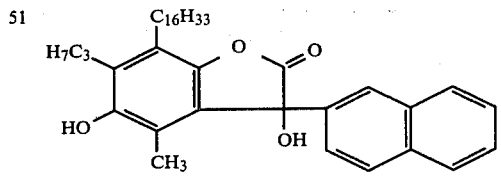
52 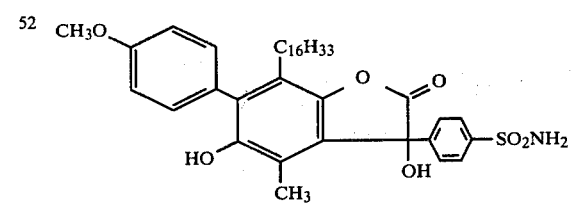
53 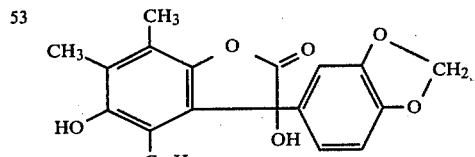
54 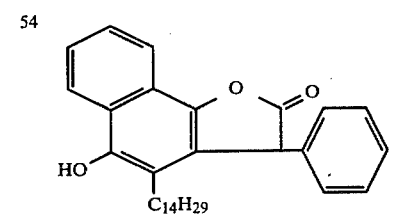
55 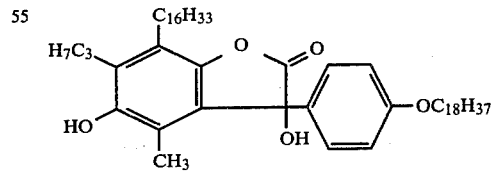
56 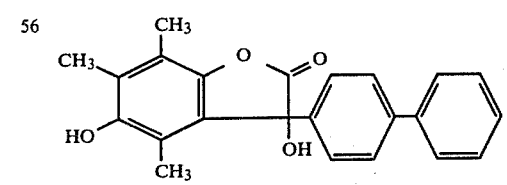
57 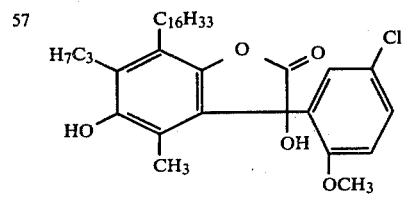

58 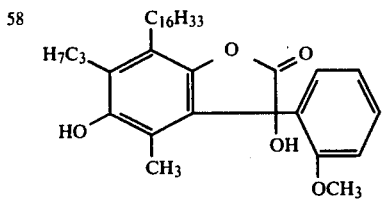

59 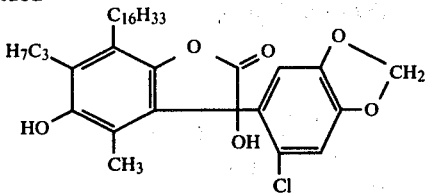

60 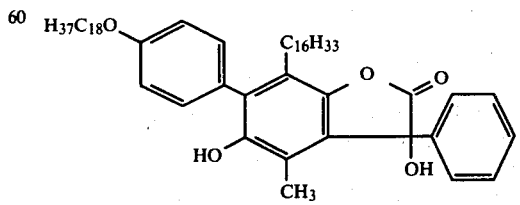

The ED precursor compounds of formula I used according to the invention are to be regarded as α-substituted α-hydroxylactones of hydroquinones containing a suitable α-OH-α-R$^1$-substituted acetic acid group. They may be prepared by the molecular addition of oxygen to appropriate lactones corresponding to the following general formula II

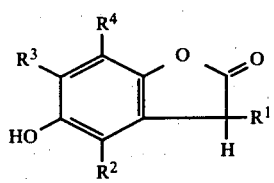

II in which R$^1$, R$^2$, R$^3$ and R$^4$ are defined as in formula I, using the method described for the preparation of triphenyl carbinol from triphenylmethane (Lit.: Russel et al., J.Amer.Chem.Soc. 84, 2652 (1962)).

The lactones of formula II are obtainable by the Michael addition of α-R$^1$-substituted acetonitriles to p-benzoquinones substituted by R$^2$, R$^3$ and R$^4$.

The acetonitriles used (e.g. benzyl cyanides) are in general obtainable commercially or can be prepared by the usual methods of organic synthesis [Lit.: (1) Houben-Weyl, Methoden der Organischen Chemie, Volume VIII, page 294, Georg-Thieme-Verlag Stuttgart, 1952; (2) Shigeliko Sugasawa, Hajime Shigehara, Chem. Ber. 74, 459 (1941)].

The required p-benzoquinones substituted with R$^2$, R$^3$ and R$^4$ have also been prepared by methods known in the literature [Lit.: (1) Houben-Weyl, Methoden der Organischen Chemie, Vol. 7/3a "Quinone I"; (2) Schill, Zuercher, Logemann, Chem.Ber. 108, 1570 (1975); (3) Kuser, Inderbitzin, Brauchli, Eugster, Helv.Chim. Acta 54, 980 (1971)].

Methods of preparation of some selected compounds are described below:

COMPOUND 1

6.6 g (0.29 mol) of sodium were dissolved in 300 ml of absolute ethanol. A solution of 59 g (0.37 mol) of diethylmalonate in 60 ml of absolute ethanol was added with stirring. After 10 minutes' stirring, a solution of 115 g (0.3 mol) of 2-methyl-5-hexadecyl-6-propyl-1,4-benzoquinone in 1300 ml of absolute ethanol was added dropwise over a period of 60 minutes. Stirring was continued for 2 hours at room temperature and the reaction mixture was left to stand overnight. It was then poured out on 5 kg of ice to which 125 ml of concentrated hydrochloric acid had been added, and the resulting precipitate was taken up in ethyl acetate. The ethyl acetate extract was thoroughly washed several times with water, dehydrated over sodium sulfate and concentrated by evaporation. The residue was stirred up with petroleum ether and suction filtered.

111 g = 75% yield were obtained; M.p. 87°–88.5° C.

COMPOUND 3

Preliminary stage

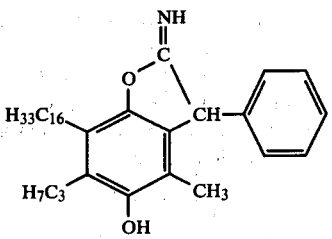

9.5 g (0.412 mol) of sodium were dissolved in 400 ml of anhydrous ethanol. A solution of 62 g (0.53 mol) of benzyl cyanide in 60 ml of anhydrous ethanol was added with stirring. After about 10 minutes' stirring and cooling to room temperature, a solution of 160 g (0.412 mol) of 2-methyl-5-hexadecyl-6-propyl-1,4-benzoquinone in 1600 ml of anhydrous ethanol was added dropwise with vigorous stirring over a period of 60 minutes. After 3 hours' stirring at room temperature, the reaction mixture was left to stand overnight and then poured out on a mixture of 5 l of ice water and 100 ml of concentrated hydrochloric acid and shaken up with ethyl acetate.

After repeated washing with water and dehydration with Na$_2$SO$_4$ sicc., the ethyl acetate extract was concentrated by evaporation on a rotary evaporator.

About 250 g of preliminary stage 1 was obtained, which was used as crude product for further reaction.

COMPOUND 3

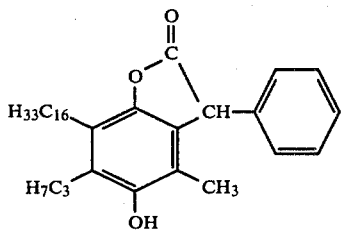

253 g of the crude product of the preliminary stage were dissolved hot in 1.5 l of acetone, and 120 ml of concentrated hydrochloric acid were added within 30 minutes with stirring. After 10 minutes' boiling under reflux, the solution was stirred into water and the resulting precipitate was shaken with ethyl acetate. The extracts were washed with water, dehydrated over $Na_2SO_4$ sicc. and evaporated to dryness on a rotary evaporator.

The residue was taken up with about 300 ml of petroleum hydrocarbon. The precipitate which formed was suction filtered and washed with petroleum hydrocarbon. Colorless crystals melting at 113° to 115° C. were obtained by recrystallization from methanol/ethyl acetate (40:3).

Yield: 127 g.

COMPOUND 4

78 g (0.154 mol) of compound 3 were dissolved in 1.25 l of a mixture of anhydrous DMSO (dimethylsulfoxide) and t-butanol (4:1) with heating and then cooled. 1.57 g of potassium t-butylate were added and about 20 l of gaseous oxygen were passed through the mixture within 60 minutes. The reaction solution was then stirred into a mixture of 4 l of water, 10 ml of glacial acetic acid and 1.5 l of ethyl acetate, and the ethyl acetate phase was separated off, washed several times with water and evaporated after dehydration over $Na_2SO_4$ sicc.

The residue was taken up in petroleum ether and the resulting precipitate was suction filtered. 52.5 g of compound 4, M.p. 99°–100° C., were obtained after recrystallization from petroleum ether.

COMPOUND 10

Stage 1: 4-Octadecyloxybenzyl cyanide

A solution of 21.5 g of sodium cyanide and 1 g of tetrabutyl ammonium bromide in 40 ml of water was added to a solution of 55 g of 4-octadecyloxybenzyl chloride in 100 ml of benzene at 50° C. and the mixture was stirred for 4 hours. The benzene layer was washed twice with water, dried and evaporated. The residue was recrystallized from petroleum ether (50° to 75° C.). Yield: 47.5 g M.p. 79°–80° C.

4-Octadecyloxybenzyl chloride required as starting material may be prepared as follows:

4-Oxybenzaldehyde is alkylated with octadecylbromide in the presence of oxygen and the resulting 4-octadecyloxybenzaldehyde (m.p. 48° to 50° C.) is reduced to 4-octadecyloxybenzyl alcohol (m.p. 83° to 85° C.) with sodium borohydride and converted into 4-n-octadecyloxybenzyl chloride (m.p. 52° to 55° C.) using hydrogen chloride in a solution in benzene.

Stage 2:
5-Hydroxy-2-imino-4,6,7-trimethyl-3-(4-octadecyloxyphenyl)-2,3-dihydro-benzo[b]furan

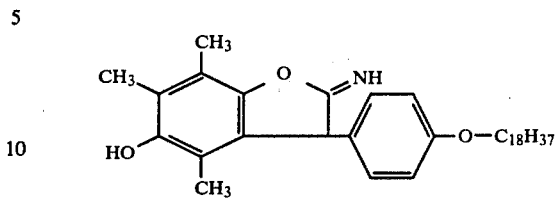

2.3 g (0.1 mol) of sodium are dissolved in 300 ml of absolute ethanol in a three-necked flask equipped with stirrer, dropping funnel and reflux condenser. After the addition of 42.3 g (0.11 mol) of "benzyl cyanide" from stage 1, the reaction mixture is heated to about 75° C. with stirring and a solution of 15 g (0.1 mol) of trimethyl-p-benzoquinone in 130 ml of absolute ethanol is added dropwise within 10 to 15 minutes. Stirring is then continued for 2 hours under conditions of slow cooling, and after the reaction mixture has been left to stand overnight, it is stirred into a mixture of 1 N HCl/ethyl acetate. The ethyl acetate layer is separated off and extracted twice with water, and the ethyl acetate solution is evaporated. The residue is worked up without further purification.

COMPOUND 10

5-Hydroxy-2-oxo-4,6,7-trimethyl-3-(4-octadecyloxyphenyl)-2,3-dihydro-benzo[b]furan

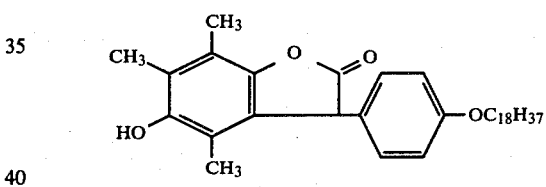

The residue from Stage 2 is dissolved in 650 ml of acetone with heating and then boiled under reflux for 30 minutes after the addition of 32 ml of concentrated hydrochloric acid. The reaction mixture is poured out on water and the organic phase is taken up with ethyl acetate, washed twice with water and drained. The residue is treated with petroleum ether and the solid product is suction filtered.

Yield: 45 g M.p.: 114°–117° C.

COMPOUND 19

26 g of Compound 10 are dissolved in 500 ml of a mixture of 4 parts of dimethylsulfoxide and 1 part of tert.-butanol. Oxygen (200 ml in 30 seconds) is passed through at 20° C. after the addition of 0.54 g of potassium tert.-butylate. The temperature is maintained at 20° C. by mild cooling. After 60 minutes, the molecular addition of oxygen is completed and the solution is poured out on 0.1 N acetic acid (1 l). After the product has been taken up in ethyl acetate and washed several times with water, the solution in ethyl acetate is evaporated and the residue is recrystallized from n-butyl chloride.

Yield: 14 g M.p. 132°–135° C.

Splitting of the lactone ring to convert the ED precursor compound into the ED compound under the conditions desired for processing is particularly important if the benzolactones used according to the invention are to be suitable for photographic purposes, in particular for dye release processes. This splitting of the lactone ring should take place at pH values of from 9 to 13 since at lower pH values it would lead to premature formation of the ED compound and hence to the formation of color fogs. If, on the other hand, splitting of the ring only takes place at pH values above 13, the ED compound forms too slowly and the times required for formation of the dye image are too long. Since the ED precursor compound and the IHR compound used in combination with it are dissolved in one of the known oil formers and the resulting solution of solutions are dispersed in the aqueous phase of the casting solution for the photographic layer so that the compounds are contained in a finely divided form in the organic phase, the pH range of from 9 to 13 indicated as suitable applies to the aqueous phase.

Benzolactone compounds used according to the invention must fulfil a second condition in addition to that indicated above. The ED compound obtained from the ED precursor compound by splitting of the lactone ring must have a redox potential which is sufficiently low. The redox potential of the ED compound, measured against a normal calomel electrode, must be smaller than $+0.255$, preferably smaller than $+0.191$ at $pH=0$. The redox potential may be measured by the usual method of IUPAC 1953 described in "Handbook for Techniques of Electrochemistry", Vol. 1, pages 5 et seq.

The capacity for hydrolysis of the lactone ring controlled by the electron accepting substituents in this ring is determined as follows:

The following organic solution is first prepared:
40 mg of the ED precursor compound
10 mg of 1-phenyl-pyrazolidone-3
10 ml of n-butanol.

This butanolic solution is subdivided into two halves and each half is dispersed in an aqueous solution having one of the following compositions:
Solution A (pH ca. 9.2)
  50 mg of potassium ferricyanide
  310 mg of boric acid
  373 mg of potassium chloride
  85 mg of sodium hydroxide
  15 ml of water
Solution B (pH ca. 13.2)
  50 mg of potassium ferricyanide
  373 mg of potassium chloride
  188 mg of sodium hydroxide
  15 ml of water.

Splitting of the lactone ring and concomitant oxidation of the hydroquinone derivative to the corresponding quinone derivative can be examined and determined continuously by spectroscopic means of or by continuous removal of a sample and thin layer chromatographic analysis. The measurements are carried out at room temperature with vigorous stirring.

It is preferred to use those ED precursor compounds having the constitution according to the invention in which splitting up and oxidation in Solution A takes place with a half life longer than 10 minutes and in Solution B with a half life of less than 10 minutes.

The values obtained with the compounds exemplified are shown below:

|  | A | B |
|---|---|---|
| Compound No. 1 | >10 min | <10 sec |
| 3 | >10 min | <10 sec |
| 4 | >10 min | <15 sec |
| 10 | >10 min | <10 sec |
| 19 | >10 min | <10 sec |

The ED precursor compounds according to the invention are preferable to the known ED compounds, e.g. ascorbyl palmitate, as well as to the known ED precursor compounds in that they can produce higher maximum color densities within a given development time and at the same time lower minimum color densities (fog). It may be left open whether the higher maximum color densities obtained are due to more ready opening of the lactone ring and hence more rapid availability of the ED compounds proper or to their higher reduction capacity or both.

Suitable non-diffusing, reducible color providing compounds which may be used in combination with the ED precursor compounds according to the invention include, for example, the so-called BEND compounds disclosed in German Offenlegungsschrift No. 2,809,716 (Bend=ballasted electron-accepting nucleophilic displacement). To release their dyes, these compounds require an intramolecular nucleophilic displacement reaction which is made possible by the reduction. Another type of non-diffusing, reducible color providing compounds which are also suitable has been disclosed in published European Patent Application No. 0,004,399.

For monochromatic processes, the color photographic recording material according to the invention contains at least one, and for processes for the production of multicolored images it generally contains at least three, image producing layer units, each of which comprises at least one light-sensitive silver halide emulsion layer and, associated with this layer, a combination of a non-diffusing, reducible color providing compound and an electron donor compound, an ED precursor compound according to the invention being used in at least one layer unit. As a rule, one of the layer units is predominantly sensitive to blue light, another to green light and a third to red light, the associated color providing compounds in each case producing image dyes of the complementary color.

By "association" and "associated" is meant that the silver halide emulsions, ED compound or ED precursor compound and color providing compound are arranged in relation to each other so that they are capable of interacting to ensure imagewise correspondence between the silver image formed and consumption of ED compound on the one hand and between the unused ED compound and the color providing compound on the other hand so that there is a resulting correspondence between the undeveloped silver halide and the imagewise distribution of diffusible dye. The light-sensitive silver halide and the combination of color providing compound and ED compound need not necessarily be present in the same layer in order to achieve this. They may be accomodated in adjacent layers both belonging to the same layer unit.

In order to ensure sufficient interaction between the color providing compound and the associated ED precursor compound, it is advisable to accommodate these two compounds of a combination in the same layer which need not, however, be the associated silver halide emulsion layer. The fact that the ED precursor compounds according to the invention are resistant to hydrolysis under neutral conditions and therefore also resistant to oxidation makes these compounds particularly suitable for use in a common emulsion (together with the color providing compound) while the usual ED compounds are too sensitive to oxidation under comparable conditions so that they cannot be used in the same emulsion as the color providing compounds.

Any method normally employed for incorporating hydrophobic compounds in photographic layers may be used for incorporating the ED precursor compounds according to the invention. These include the usual emulsification techniques, e.g. methods by which photographic auxiliary substances are added to casting solutions in the form of emulsions with the aid of so-called oil formers. It is advisable to avoid any methods in which alkalies must be used.

The non-diffusing, reducible color providing compound is generally used in a sufficient quantity in a layer to produce a color image having the highest possible maximum color density, e.g. a quantity of from 1 to $20 \cdot 10^{-4}$ mol/m$^2$. The quantity of ED precursor compound according to the invention is adapted to the quantity of color providing compound and should be sufficient to produce as high as possible a maximum color density, i.e. to achieve as far as possible complete reduction of the color providing compound. At the same time, the quantity should not be substantially higher than is necessary for this purpose, so that the reducing agent produced from the compound in the exposed areas can, as far as possible, be used up completely by development of the exposed silver halide. The most suitable proportions of silver halide to ED precursor compound and color providing compound used in the individual case can be determined by routine tests. Suitable results may be obtained when, for example, the ED precursor compound is present in 1 to 5 times the molar quantity of the color providing compound. Suitable proportions of silver halide to associated color providing compound are approximately within the range of from 2 to 20 mol of silver halide per mol of color providing compound.

Separating layers are advantageously arranged between the different layer units. These separating layers may contain compounds which react with diffusible development products to prevent their diffusion from one layer unit to another and thereby restrict the association between different substances to one layer unit. Suitable compounds of this type are known and include, for example, non-diffusing hydroquinone derivatives as well as the so-called "scavenger compounds" described in the publication, "Research Disclosure No. 17 842" (February 1979). The ED precursor compounds according to the invention may also take over this function if they are incorporated in a separating layer between different layer units. The interaction between the exposed silver halide and the non-diffusing ED compound produced from the non-diffusing ED precursor compound according to the invention under the conditions of alkaline development is generally effected by the oxidized form of the silver halide developer used. This developer is oxidized imagewise during development and its oxidation product is capable of oxidizing the ED compound, thereby removing it from the reaction with the color providing compound. The interaction between the unoxidized ED compound and the color providing compound is direct.

Typical suitable electron transferring agents include, for example, hydroquinone compounds such as hydroquinone, 2,5-dichlorohydroquinone and 2-chlorohydroquinone; aminophenol compounds such as, for example, 2-aminophenol, N-methylaminophenol, 3-methyl-4-aminophenol and 3,5-dibromoaminophenol; pyrocatechol compounds such as, for example, pyrocatechol, 4-cyclohexyl pyrocatechol, 3-methoxypyrocatechol and 4-(N-octadecylamino)-pyrocatechol; and phenylene diamine compounds such as, for example, N,N-diethyl-p-phenylenediamine, 3-methyl-N,N-diethyl-p-phenylenediamine, 3-methoxy-N-ethyl-N-hydroxyethyl-p-phenylenediamine and N,N,N',N'-tetramethyl-p-phenylenediamine.

According to a particularly advantageous embodiment of the invention, a 3-pyrazolidone compound is used as electron transferring agent, such as, for example, the following: 1-Phenyl-3-pyrazolidone; 1-phenyl-4,4-dimethyl-3-pyrazolidone; 4-hydroxymethyl-4-methyl-1-phenyl-3-pyrazolidone; 1-p-tolyl-3-pyrazolidone; 1-phenyl-4-methyl-3-pyrazolidone; 1-phenyl-5-methyl-3-pyrazolidone; 1-phenyl-4,4-bis-(hydroxymethyl)-3-pyrazolidone; 1,4-dimethyl-3-pyrazolidone; 4-methyl-3-pyrazolidone; 4,4-dimethyl-3-pyrazolidone; 1-(3-chlorophenyl)-4-methyl-3-pyrazolidone; 1-(4-chlorophenyl-4-methyl-3-pyrazolidone; 1-(3-chlorophenyl)-3-pyrazolidone; 1-(4-chlorophenyl)-3-pyrazolidone; 1-(4-tolyl)-4-methyl-3-pyrazolidone; 1-(2-tolyl)-4-methyl-3-pyrazolidone; 1-(4-tolyl)-4-hydroxymethyl-4-methyl-3-pyrazolidone; 1(3-tolyl)-3-pyrazolidone; 1-(3-tolyl)-4,4-dimethyl-3-pyrazolidone; 1-(2-trifluoroethyl)-4,4-dimethyl-3-pyrazolidone and 5-methyl-3-pyrazolidone.

A combination of different electron transferring agents may also be used, e.g. a combination as described in U.S. Pat. No. 3,039,869.

The developer compounds may be used in the development liquid or they may be at least partially accommodated in any layer of the photographic recording material, e.g. in one or more silver halide emulsion layers, in layers in which the color providing compounds are accommodated, in intermediate layers or in image receiving layers.

The optimum electron transferring compound for any individual case depends, of course, on the ED compound used as well as on the non-diffusing reducible color providing compound and on the conditions employed for development of the recording material.

For carrying out the dye diffusion transfer process, there is generally used a light-sensitive element containing one or more silver halide emulsion layer units and non-diffusing color providing compounds and ED compounds or their purecursors associated with these units, and an image receiving element in which the desired color image is produced by imagewise transfer of diffusible dyes. In order to effect this transfer, firm contact must be established between the light-sensitive element and the image receiving element, for at least a finite period of time within the development time, so that the imagewise distribution of diffusible dyes produced by development in the light-sensitive element can be transferred to the image receiving element. This contact may be established after development has started or it may already have been established before development. The latter is the case when, for example, the dye diffusion transfer process is carried out using a so-called integral recording material in which the light-sensitive element and the image receiving element form an integral unit, hereinafter referred to as monosheet material, which is maintained as a unit even after completion of development, i.e. the light-sensitive element is not separated from the image receiving element even after transfer of the dye. Such an arrangement has been described in, for example, German Offenlegungsschrift No. 2,019,430.

The image receiving element may thus be a component of the color photographic recording material, e.g. it may be in the form of an image receiving layer arranged on a transparent support underneath the light-sensitive silver halide emulsion layer units. A light impervious, preferably light reflecting layer of binder is then suitably arranged between the image receiving layer and the light-sensitive layers. The image receiving layer, which in another form of the dye transfer process may also be arranged on a separate support (image receiving sheet), generally contains, in known manner, a basic mordant for diffusible anionic (acid) dyes.

The compounds used as mordants for acid dyes are preferably long chain quaternary ammonium or phosphonium compounds or tertiary sulfonium compounds, e.g those described in U.S. Pat. Nos. 3,271,147 and 3,271,148. Certain metal salts and their hydroxides which form difficultly soluble compounds with the acid dyes may also be used. The dye mordants are dispersed in one of the usual hydrophilic binders in the receiving layer, e.g. in gelatine, polyvinyl pyrrolidone or partially or completely hydrolysed cellulose esters. Some binders may, of course, also function as mordants, e.g. copolymers or polymer mixtures of vinyl alcohol and N-vinylpyrrolidone, for example as described in German Auslegeschrift No. 1,130,284, and polymers of quaternary bases containing nitrogen, e.g. polymers of N-methyl-2-vinylpyridine, as described, for example, in U.S. Pat. No. 2,484,430. Other useful mordanting binders include, for example, guanyl hydrazone derivatives of alkyl vinyl ketone polymers such as those described in U.S. Pat. No. 2,882,156 and guanyl hydrazone derivatives of acyl styrene polymers as described, for example, in German Offenlegungsschrift No. 2,009,498.

As a general rule, however, other binders, e.g. gelatine, would be added to the last mentioned mordanting binders. Other polymeric mordants have been described, for example, in U.S. Pat. No. 3,709,690 and German Offenlegungsschriften Nos. 2,315,304; 2,445,782; 2,551,786 and 2,631,521.

The color photographic recording material according to the invention may in addition contain acid layers and so-called retarding layers which together form a so-called integral neutralization system. Such a system may be arranged in known manner between the support layer and the image receiving layer on it or it may be arranged in some other position in the layer combination, e.g. above the light-sensitive layers, i.e. remote from these light-sensitive layers when viewed from the image receiving layer. The neutralization system is normally arranged so that the retarding layer is situated between the acid layer and the position where the alkaline development liquid or paste comes into operation. Such acid layers, retarding layers or neutralization systems consisting of both have been disclosed in, for example, U.S. Pat. Nos. 2,584,030; 2,983,606; 3,362,819 and 3,362,821 and German Offenlegungsschriften Nos. 2,455,762; 2,601,653; 2,716,505 and 2,816,878. Such a neutralization system may also contain two or more retarding layers, in known manner.

In a particular embodiment, the recording material according to the invention may contain one or more pigment containing opaque layers which are permeable to aqueous liquids. These layers may fulfil two functions: They may prevent unwanted access of light to light-sensitive layers and secondly, they may form an aesthetically pleasing background for the color image produced, particularly if the pigment contained in them is a light or white pigment such as $TiO_2$. Integral color photographic recording materials having such a pigment layer have been disclosed, for example in U.S. Pat. No. 2,543,181 and German Auslegeschrift No. 1,924,430. Instead of providing a previously formed opaque layer, means may be provided to produce such a layer during the development process. In conformity with its two functions mentioned above, such a pigment layer may be built up of two or more partial layers, one of which may contain, for example, a white pigment and the other may contain, for example, a dark, light-absorbent pigment, e.g. carbon black.

In a particularly preferred embodiment of the invention, the photographic material is an integral color photographic recording material for carrying out the dye diffusion transfer process and comprises, for example, the following layer elements:

(1) a transparent support layer
(2) an image receiving layer
(3) a light-impervious layer
(4) a light-sensitive element having at least one light-sensitive silver halide emulsion layer, at least one non-diffusible color providing compound associated with this layer and an ED precursor compound
(5) a retarding layer
(6) an acid polymer layer
(7) a transparent support layer.

The monosheet material may consist of two parts prepared separately from each other, namely the light-sensitive part (layer elements 1 to 4) and the cover sheet (layer elements 5 to 7) which are then placed with their active surfaces in contact and joined together, optionally using spacer strips so that a space is formed between the two parts for receiving an accurately measured quantity of development liquid. The layer elements 5 and 6, which together form the neutralization system, additionally or alternatively may also be arranged between the support layer and the image receiving layer of the light-sensitive element although in reverse sequence.

Means may also be provided for introducing a development liquid between the light sensitive part and the cover sheet, e.g. in the form of a container placed laterally which can be split open by mechanical forces to pour out its contents between two adjacent layers of the monosheet material.

The developer preparation may contain developer compounds in addition to the aqueous alkali, but these developer compounds must be adjusted to the nature of the color producing compounds. Other components of the developer preparation include thickeners for increasing the viscosity, e.g. hydroxyethylcellulose, silver halide solvents, e.g. sodium thiosulfate or one of the bis-sulfonylalkane compounds described in German Offenlegungsschrift No. 2,126,661, and clouding agents for producing opaque layers, e.g. pigments of $TiO_2$, ZnO, barium stearate or kaolin. Alternatively or in addition, some of these constituents may be incorporated in one or more layers of the color photographic recording material according to the invention.

EXAMPLES

A layer of mordant, a light-reflective layer and a light-sensitive silver halide emulsion layer were applied, in that order, to a transparent support layer of cellulose triacetate.

Mordant layer 3.75 g of a copolymer of one part of styrene and one part of maleic acid imide of N,N-dimethyl-N-hexadecyl-N-ω-aminopropyl-ammonium bromide were dissolved in 15 ml of ethanol and the solution obtained was stirred into 75 ml of a 5% gelatine solution and homogenized. After the addition of 2.6 ml of a 5% saponin solution and 1 mol of a 2% mucochloric acid solution, the resulting solution was adjusted to the usual viscosity for casting (ca. 11 mPa.s) and applied to the support by immersion at 40° C. (casting speed 5 m/min).

Light-reflective layer

A slurry of 42 g of $TiO_2$ in 20 ml of water was dispersed in 150 ml of an 8% aqueous gelatine solution with the addition of 5 ml of a 5% aqueous solution of sodium dodecyl benzene sulfonate and 5 ml of a 5% aqueous saponin solution. After the addition of 1 ml of a 2% mucochloric acid solution, the dispersion was adjusted to a viscosity of 13 mPa.s at 40° C. and applied to the dried mordant layer by the immersion process (casting speed 5 m/min).

Silver halide emulsion layer 1 mMol of non-diffusing color providing compound (dye releaser) and 1.5 mMol of ED precursor compound were dissolved in 5 ml of ethyl acetate. After the addition of 2 mol of palmitic acid diethylamide, the solution was emulsified in 25 ml of a 5% gelatine solution with the addition of 5 ml of a 5% aqueous solution of sodium dodecylbenzene sulfonate using a Bühler homogeniser at ca. 1000 revs/min. The emulsion was filtered through a fluted filter paper and made up to 75 ml with 5% gelatine solution.

After the addition of 1 mol of a 2% mucochloric acid solution, 32 g of a silver iodobromide emulsion which was ready for casting were added to the emulsion described above. This silver iodobromide emulsion had been prepared using 74 g of $AgNO_2$/kg of emulsion. It had an Ag/gelatine ratio of 1:1.1. The silver bromide emulsion contained 0.67 mol % of silver iodide.

The mixtures were applied to the support described above the immersion process at a speed of 5 m/min and at ca. 40° C.

After 24 hours' drying, the various samples were exposed on the emulsion side through a grey step filter and developed with a developer paste of the composition described below applied in a thickness of about 300 μm. Development was carried out for 2 minutes at 18° C. and stopped for 2 minutes in a 5% acetic acid solution and the samples were then briefly washed and dried.

Developer 20 g of carbethoxymethylcellulose were dissolved in 800 ml of water with stirring.

40 g of solid sodium hydroxide, 1.5 g of the sodium salt of ethylene diaminotetracetic acid, 11.5 g of borax, 1 g of sodium hexametaphosphate, 3 g of potassium bromide 1.6 g of 1-phenyl-4-methyl-4-hydroxymethyl-pyrazolidone-3 and 0.1 g of 1-phenyl-5-mercapto-tetrazole were added to the homogeneous solution. The solution was then made up to 1000 ml with water and adjusted to a pH of 13.2-13.3 by the addition of 30 ml of glacial acetic acid.

The following color providing compounds were used for the comparison described below:

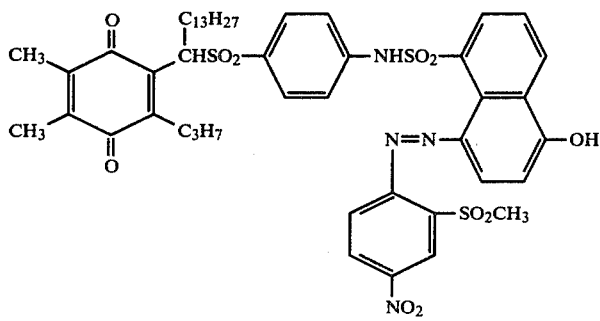

A

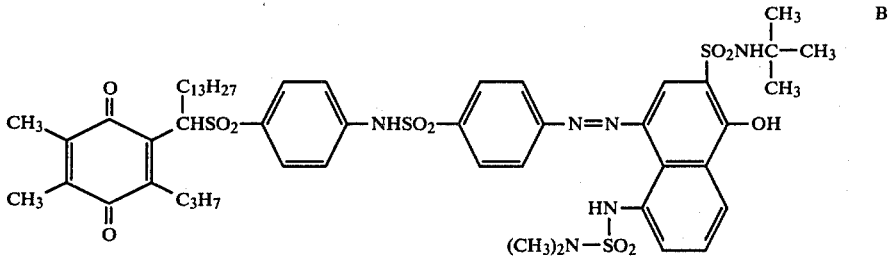

B

-continued

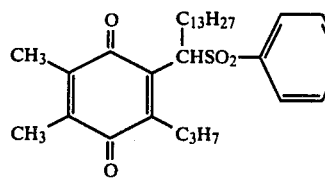
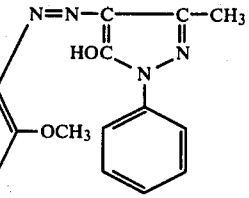

C

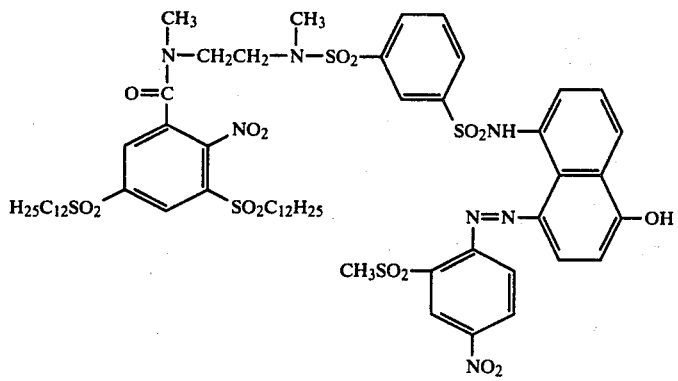

D

Compound E was used as prior art ED precursor compound for comparison (German Offenlegungsschrift No. 2,806,716):

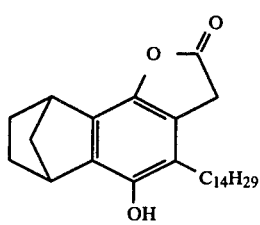

E

The following combinations were tested for the $D_{min}/D_{max}$ obtainable:

| Dye | ED precursor | $D_{min}$ | $D_{min}$ |
|---|---|---|---|
| A | E | 0.04 | 0.60 |
|  | 1 | 0.10 | 1.42 |
|  | 3 | 0.05 | 1.28 |
|  | 4 | 0.04 | 1.92 |
|  | 11 | 0.02 | 1.25 |
|  | 17 | 0.02 | 2.02 |
|  | 10 | 0.02 | 1.08 |
|  | 19 | 0.02 | 1.98 |
| B | E | 0.02 | 0.06 |
|  | 1 | .02 | 1.40 |
|  | 3 | 0.02 | 1.05 |
|  | 4 | 0.04 | 1.72 |
|  | 6 | 0.04 | 1.85 |
|  | 20 | 0.02 | 1.12 |
|  | 29 | 0.04 | 1.73 |
|  | 5 | 0.02 | 1.56 |
|  | 12 | 0.05 | 1.95 |
| C | E | 0.0 | 0.06 |
|  | 3 | 0.02 | 0.72 |
|  | 4 | 0.0 | 0.94 |
|  | 10 | 0.02 | 0.82 |
|  | 19 | 0.01 | 1.06 |
| D | 3 | 0.06 | 0.95 |
|  | 4 | 0.10 | 1.95 |
|  | 18 | 0.08 | 0.92 |
|  | 53 | 0.10 | 1.64 |

A and D were measured behind a red filter, B behind green filter and C behind blue filter.

We claim:

1. Color photographic recording material having at least one light-sensitive silver halide emulsion layer and, associated thereto, a non-diffusing electron donor precursor compound (ED precursor compound) from which a non-diffusing ED compound is formed under alkaline development conditions, wherein the improvement comprises said ED precursor compound is a compound of the following general formula

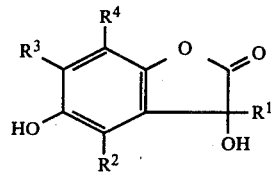

in which $R^1$ represents a carbocyclic or heterocyclic aromatic group, $R^2$, $R^3$ and $R^4$ which may be the same or different substituents, represent hydrogen, alkyl, alkenyl, aryl, alkoxy, alkylthio or amino, or $R^3$ and $R^4$ together complete a condensed carbocyclic ring, and at least one of the substituents $R^1$, $R^2$, $R^3$ and $R^4$, contains a ballast group having 10 to 22 carbon atoms which confers diffusion resistance.

2. Color photographic recording material having at least one light-sensitive silver halide emulsion layer and, associated thereto, a combination of a non-diffusing, reducible color providing compound which in its reduced and under alkaline development conditions releases a diffusing dye or dye precursor compound, and a non-diffusing electron donor precursor compound (ED precursor compound) from which a non-diffusing electron donor compound (ED compound) is formed under alkaline development conditions, which ED compound reduces the non-diffusing, color providing compound under alkaline development conditions wherein the improvement comprises said ED precursor compound is a compound of the following general formula:

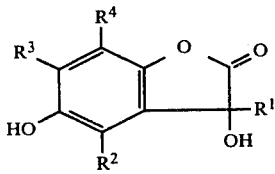

in which
R¹ represents a carbocyclic or heterocyclic aromatic group,
R², R³ and R⁴ which may be the same or different substituents, represent hydrogen, alkyl, alkenyl, aryl, alkoxy, alkylthio or amino, or
R³ and R⁴ together complete a condensed carbocyclic ring,
and at least one of the substituents R¹, R², R³ and R⁴ contains a ballast group having 10 to 22 carbon atoms which confers diffusion resistance.

3. Material as claimed in claim 2, in which R¹ is a phenyl group.

4. Material as claimed in claim 2, in which each of the non-diffusing reducible color providing compound and the ED precursor compound is contained in a layer of the material in form of a heterodisperse distribution of a solution in an oil former.

5. Material as claimed in claim 4, in which both, the non-diffusing reducible color providing compound and the ED precursor compound are contained in a layer of the material in form of a heterodisperse distribution of a common solution in an oil former.

6. Material as claimed in claim 4, in which the oil former is a dialkylamide of an alkane carboxylic acid having 8 to 22 C-atoms.

7. Material as claimed in claim 6, in which the oil former is a dialkylamide of lauric or palmitic acid.

* * * * *